United States Patent
Zhang (10) Patent No.: US 8,858,443 B2
(45) Date of Patent: Oct. 14, 2014

(54) SYSTEM FOR CARDIAC ULTRASOUND IMAGE ACQUISITION

(75) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1128 days.

(21) Appl. No.: 12/706,106

(22) Filed: Feb. 16, 2010

(65) Prior Publication Data

US 2010/0210945 A1 Aug. 19, 2010

Related U.S. Application Data

(60) Provisional application No. 61/153,067, filed on Feb. 17, 2009.

(51) Int. Cl.
- *A61B 8/00* (2006.01)
- *A61B 6/00* (2006.01)
- *A61B 8/08* (2006.01)
- *A61B 5/0205* (2006.01)

(52) U.S. Cl.
CPC . *A61B 8/08* (2013.01); *A61B 6/466* (2013.01); *A61B 5/0205* (2013.01); *A61B 8/5238* (2013.01); *A61B 8/4472* (2013.01); *A61B 8/543* (2013.01); *A61B 8/0883* (2013.01)
USPC ............................ 600/443; 600/407; 600/437

(58) Field of Classification Search
CPC ..... A61B 8/4472; A61B 8/5238; A61B 8/543
USPC .......................................... 600/407, 437, 443
See application file for complete search history.

(56) References Cited

U.S. PATENT DOCUMENTS

| | | | |
|---|---|---|---|
| 5,152,290 A | 10/1992 | Freeland | |
| 5,846,202 A | 12/1998 | Ramamurthy et al. | |
| 5,876,345 A * | 3/1999 | Eaton et al. | 600/466 |
| 5,993,390 A * | 11/1999 | Savord et al. | 600/437 |
| 6,168,564 B1 * | 1/2001 | Teo | 600/443 |
| 6,224,553 B1 | 5/2001 | Nevo et al. | |
| 6,306,095 B1 | 10/2001 | Maslak | |
| 6,390,982 B1 | 5/2002 | Bova et al. | |
| 6,488,629 B1 | 12/2002 | Saetre | |
| 6,510,337 B1 * | 1/2003 | Heuscher et al. | 600/428 |
| 6,626,831 B2 | 9/2003 | Maslak | |
| 6,673,018 B2 | 1/2004 | Friedman et al. | |
| 6,824,518 B2 | 11/2004 | von Behren et al. | |
| 7,314,446 B2 * | 1/2008 | Byrd et al. | 600/443 |

(Continued)

*Primary Examiner* — Tse Chen
*Assistant Examiner* — Jason Ip
(74) *Attorney, Agent, or Firm* — Brennan K Bradley (57) ABSTRACT

An ultrasound image acquisition device initiates acquisition of anatomical images of a portion of patient anatomy in response to a heart rate related synchronization signal. The ultrasound image acquisition device includes multiple ultrasound transducers for generating sound waves. The ultrasound transducers are arranged in different transducer groups oriented to enable acquisition of different ultrasound imaging information used in generating a single composite ultrasound image. A synchronization processor derives the heart rate related synchronization signal from a patient cardiac function blood flow related parameter. The synchronization signal enables adaptive activation of a particular group of the different transducer groups for acquisition of ultrasound imaging information used in generating the single composite ultrasound image. A display processor presents the single composite ultrasound image, acquired by the ultrasound image acquisition device, to a user on a reproduction device.

16 Claims, 9 Drawing Sheets

(56) References Cited

U.S. PATENT DOCUMENTS

| | | |
|---|---|---|
| 7,542,794 B1 | 6/2009 | Zhang et al. |
| 8,073,211 B2 * | 12/2011 | Halmann .................. 382/128 |
| 2004/0039286 A1 | 2/2004 | Kuban et al. |
| 2005/0197572 A1 | 9/2005 | Williams et al. |
| 2005/0267453 A1 | 12/2005 | Wong et al. |
| 2006/0155192 A1 | 7/2006 | Rasmussen |
| 2008/0170654 A1 | 7/2008 | Tkaczyk et al. |
| 2008/0177181 A1 | 7/2008 | Hastings |

* cited by examiner

SYSTEM FOR CARDIAC ULTRASOUND IMAGE ACQUISITION

This is a non-provisional application of provisional application Ser. No. 61/153,067 filed Feb. 17, 2009, by H. Zhang.

FIELD OF THE INVENTION

This invention concerns an ultrasound medical imaging system for adaptively acquiring anatomical images involving activating different transducer groups for acquisition of ultrasound imaging information presented in a composite ultrasound image.

BACKGROUND OF THE INVENTION

Ultrasound medical imaging is used for imaging the heart and surrounding intra-thoracic structures. However known ultrasound image scanning and acquisition systems typically employ a fixed time interval between frames and fail to effectively scan for optimum imaging results for real time clinical monitoring and diagnosis. Known systems employ surface ECG signals for image gating to avoid cardiac contraction noise, for example, but offer limited gating capability for studying particular cardiac functions. Continuous image scanning and acquisition, such as intra-cardiac ultrasound imaging is used to study cardiac operation and treatment. However, known systems fail to comprehensively perform cardiac function tracking of maximum size and volume of ventricle chambers, for example, in the presence of cardiac tissue movement.

Known intra-cardiac ultrasound imaging usually captures a tissue dynamic image with 30-60 frames per second (fps) speed. However cardiac depolarization and repolarization, such as a QRS complex and contraction procedure are desirably imaged at a higher speed for accurate determination of detail of cardiac pathology changes. In known ultrasound systems, the time interval between image frame acquisition is typically equal and fixed (uniform scanning). This may result in missing capture of a fast contraction image frame, such as EoS (end of systolic) and EoD (end of diastolic) time image frame. In known systems for performing continuous ultrasound imaging, the image resolution, scanning speed/rate and sensitivity is not controllable once an image scanning procedure is initiated. Some known systems employ faster, multichannel (crystal) intra-cardiac ultrasound image scanning with high power (intensity). These systems may over heat intra-cardiac ultrasound sensors and a catheter and may over scan (perform redundant scanning) without capturing useful information, such as during rest time of a heart cycle. Further because of an upper limit on ultrasound image scanning speed, intra-cardiac ultrasound may be distorted by cardiac contraction, patient movement, and other bio-noise (such as respiration). A system according to invention principles addresses these deficiencies and related problems.

SUMMARY OF THE INVENTION

An ultrasound medical imaging system automatically determines image resolution, scanning frequency and acquisition speed in response to data indicating a clinical application and cardiac function signals including hemodynamic (blood pressure) signals and vital sign (such as SPO2, respiration, NIBP) signals used to trigger and synchronize image scanning and data acquisition. An ultrasound medical imaging system adaptively acquires anatomical images using an ultrasound image acquisition device. The ultrasound image acquisition device initiates acquisition of anatomical images of a portion of patient anatomy in response to a heart rate related synchronization signal. The ultrasound image acquisition device includes multiple ultrasound transducers for generating sound waves. The ultrasound transducers are arranged in different transducer groups oriented to enable acquisition of different ultrasound imaging information used in generating a single composite ultrasound image. A synchronization processor derives the heart rate related synchronization signal from a patient cardiac function blood flow related parameter. The synchronization signal enables adaptive activation of a particular group of the different transducer groups for acquisition of ultrasound imaging information used in generating the single composite ultrasound image. A display processor presents the single composite ultrasound image, acquired by the ultrasound image acquisition device, to a user on a reproduction device.

DETAILED DESCRIPTION OF THE INVENTION

A system improves medical imaging using non-uniform and nonlinear cardiac functional signals such as hemodynamic signals (invasive blood pressure, non-invasive blood pressure, blood flow speed), electrophysiological signals (surface ECG, intra-cardiac electrograms, both unipolar and bipolar signals), and vital signs signals (SPO2, respiration), to trigger and synchronize image scanning and data acquisition. The image resolution, scanning frequency and acquisition speed of the ultrasound image system is automatically determined in response to cardiac functions and a clinical application. The system uses ultrasound imaging for better quantitative and qualitative diagnosis and characterization of cardiac function and patient health status.

The system image gating and synchronization function is advantageously adaptively dynamically configured to use one or a combination of signals for different kinds of clinical applications and procedures. The combination of signals include, for example, blood pressure (hemodynamic) signals and a signal derived from heart chamber size or volume estimation. The clinical applications and procedures include an intra-cardiac blood pressure based 3D image reconstruction application and intra-cardiac electrograms (electrophysiological) and vital signal based motion tolerance ultrasound image acquisition applications. The system optimizes image frame acquisition time for image scanning and data acquisition and employs image gating for synchronization based on heart functions, such as cardiac systolic and diastolic functions which may require different speeds for image scanning and acquisition. The gating reduces over heating risk associated with continuous intra-cardiac ultrasound imaging and reduces need to adaptively adjust scanning speed and improves continuous ultrasound image acquisition.

The system advantageously provides non-uniform (controllable and function adaptive) time interval image scanning to improve continuous capture of cardiac function detail and tissue movement. The system facilitates EoD and EoS based maximum ventricle volume calculation and analysis by using precise cardiac function gating and synchronization to acquire a series of cardiac images each having the same particular time stamp. The time stamp identifies a particular point in a heart cycle that starts from a designated time origin (time equals zero) heart cycle point. The system facilitates 3D ultrasound image reconstruction of a particular cardiac function with the same particular time stamp in different cardiac cycles. In contrast, known ultrasound image scanning in 3D provides a reconstructed image typically involving substantial deviation and distortion resulting from combining images with different time stamps. The system is usable with a multi-channel intra-cardiac ultrasound transducer and catheter capable of adaptive adjustment and modification during real time continuous scanning.

Figure 1:
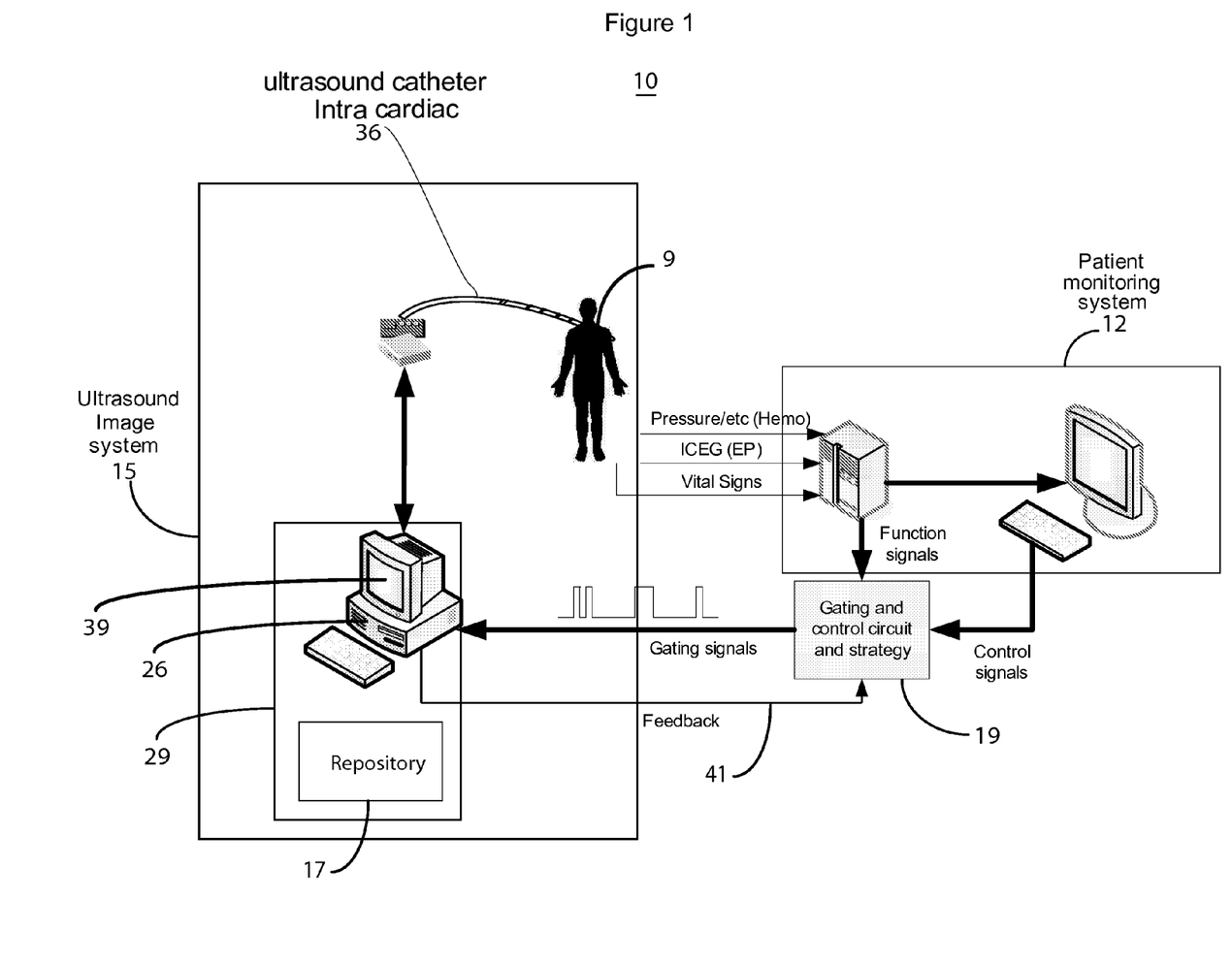
FIG. 1 shows an ultrasound medical imaging system for adaptively acquiring anatomical images, according to invention principles.

FIG. 1 shows ultrasound medical imaging system 10 for adaptively acquiring anatomical images. System 10 integrates image scanning system 15 including computer 29, with real time patient signal monitoring and recording system 12 which provides patient monitoring signals including cardiac function signals used by synchronization processor 19 to control and manipulate image scanning and acquisition. The patient monitoring signals (such as invasive blood pressure signals) provided by system 12 are used by synchronization processor 19 to generate gating and triggering signals employed by ultrasound imaging system 15 to synchronize ultrasound image scanning and acquisition with a cardiac function. A gating trigger signal provided by processor 19 using a patient monitoring system signal may be uniform or non-uniform depending on clinical application. A feedback signal 41 provided by imaging system 15 is used by processor 19 in providing gating signals compensating for circuit delay and other sources of delay.

Ultrasound image acquisition catheter device 36 initiates acquisition of anatomical images of a portion of patient 9 anatomy in response to a heart rate related synchronization signal. Device 36 includes multiple ultrasound transducers for generating sound waves. The multiple ultrasound transducers are arranged in different transducer groups and oriented to enable acquisition of different ultrasound imaging information used in generating a single composite ultrasound image. Synchronization processor 19 derives the heart rate related synchronization signal from a patient cardiac function blood flow related parameter. The synchronization signal enables adaptive activation of a particular group of the different transducer groups for acquisition of ultrasound imaging information used in generating the single composite ultrasound image. Display processor 26 presents the single composite ultrasound image, acquired by the ultrasound image acquisition device, to a user on a reproduction device 39.

Figure 2:
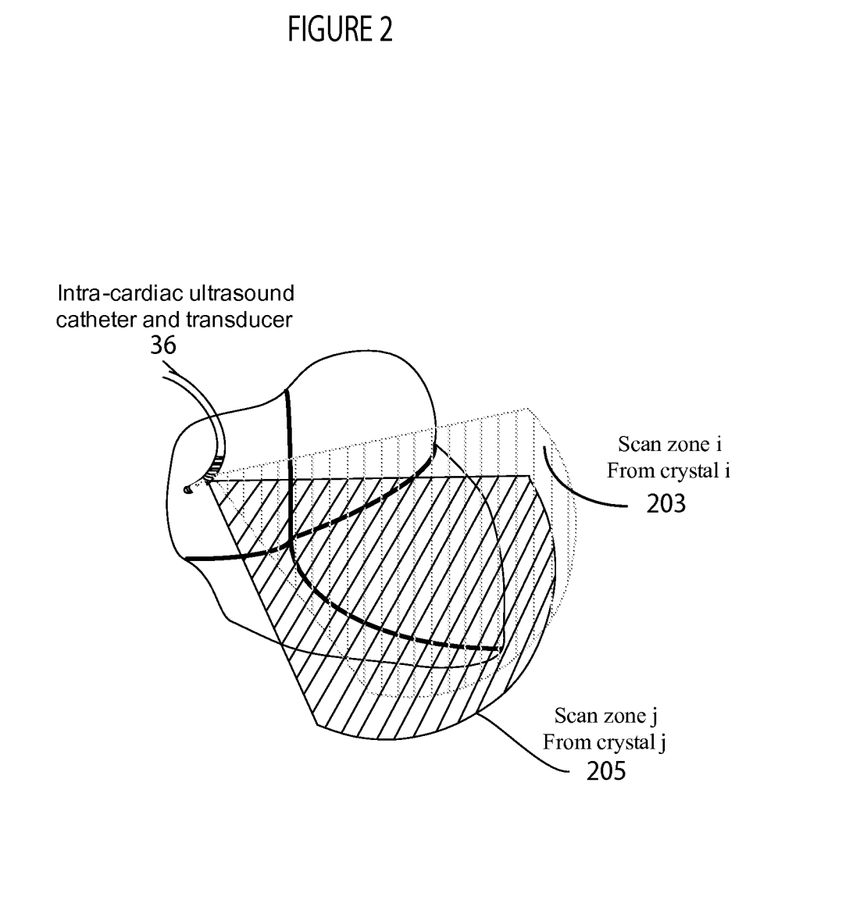
FIG. 2 shows a multi-channel intra-cardiac ultrasound catheter having different ultrasound scanning regions, according to invention principles.

FIG. 2 shows a multi-channel intra-cardiac ultrasound catheter 36 comprising a multi-channel crystal based intra-cardiac ultrasound imaging device having different ultrasound scanning regions. Specifically, catheter 36 has a first scan zone i 203 provided by crystal i and a second scan zone j 205 provided by crystal j. A transducer as used herein comprises one or more ultrasound generation crystals in a group, for example. A 32-64 channel ultrasound transducer is typically used in obtaining an intra-cardiac ultrasound image, with penetration up to 16 centimeters. Theoretically, the time for an ultrasound echo to travel 16 cm and return is around 1 ms, which provides adequate time resolution in acquisition of an ultrasound image of a cardiac function that usually is longer than 3-5 ms in duration, such as P wave or QRS complex.

Figure 3:
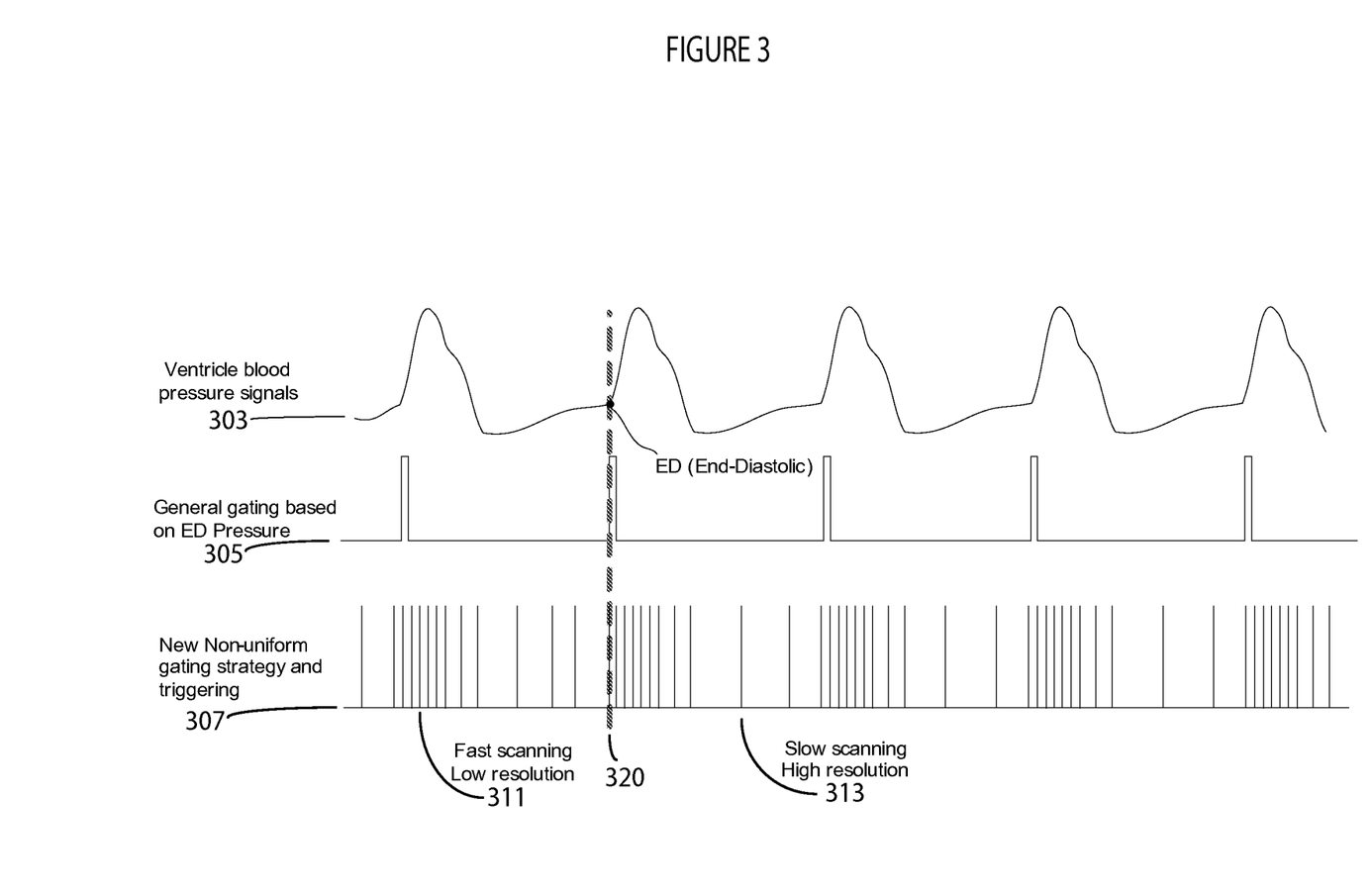
FIG. 3 illustrates non-uniform ultrasound imaging in response to invasive blood pressure of a left ventricle, according to invention principles.

FIG. 3 illustrates adaptive non-uniform ultrasound imaging performed by system 10 (FIG. 1) in response to measured invasive blood pressure of a left ventricle. In clinical hemodynamic and EP monitoring in hospital, invasive blood pressure (indicated by a hemodynamic signal) reflecting change in heart tissue and function is typically used for monitoring internal blood pressure of cardiac chambers. An EoD (end of diastolic) phase gating signal 305 is generated by processor 19 from pressure waveform 303 showing systolic and diastolic pressure switching in a cardiac cycle. Synchronization processor 19 derives synchronization waveform 307 using EoD (end of diastolic) phase gating signal 305 including leading edge synchronize pulse 320. During systolic stages, cardiac tissue is squeezing and there is substantial movement, which may be advantageously acquired using fast image scanning and data acquisition, such as for tracking valve functionality and tissue contraction mode and pattern. Also for a diastolic procedure of a cardiac cycle, blood is filling a chamber and cardiac tissue is much less dynamic and slow image scanning is sufficient to capture cardiac function information. The hemodynamic function signal based image scanning efficiently captures cardiac cycle, systolic and diastolic procedures. During a systolic stage, the heart is in a fast squeezing and contracting mode requiring relatively fast image scanning and low image resolution triggering 311 within synchronization waveform 307. During a diastolic stage, relatively slow scanning and high resolution imaging triggering 313 within synchronization waveform 307 is sufficient. Resolution as used herein means pixel resolution of an acquired image and corresponding image data processing resolution.

Synchronization processor 19 generates a synchronization waveform for gated ultrasound image acquisition of maximum and minimum volume of a ventricle (corresponding to EoD and EoS points) in a cardiac cycle using time stamps. System 10 adaptively employs different types of non-uniform ultrasound image scanning including, non-uniform triggering by time for all or a substantial portion of all crystals of an ultrasound catheter in response to a signal identifying a particular cardiac function time. System 10 uses non-uniform triggering of sequential crystals in response to a signal identifying a particular cardiac function time in a particular cardiac region. Ultrasound systems have multiple channel crystals (e.g., 80-128 channel crystals) for fast scanning speed (for example, from 30 fps (frames per second) to 100 fps, or higher). Power applied to ultrasound crystals to increase sound intensity may be increased to increase the sensitivity and quality of an intra-cardiac ultrasound image. However this may increase safety concerns. Usually a thermister is used at the tip of an intra-cardiac ultrasound transducer, however heat generation may not be uniform and result in local over-heating of a multi-channel ultrasound transducer even though continuous ultrasound high intensity scanning may be unnecessary.

Figure 4:
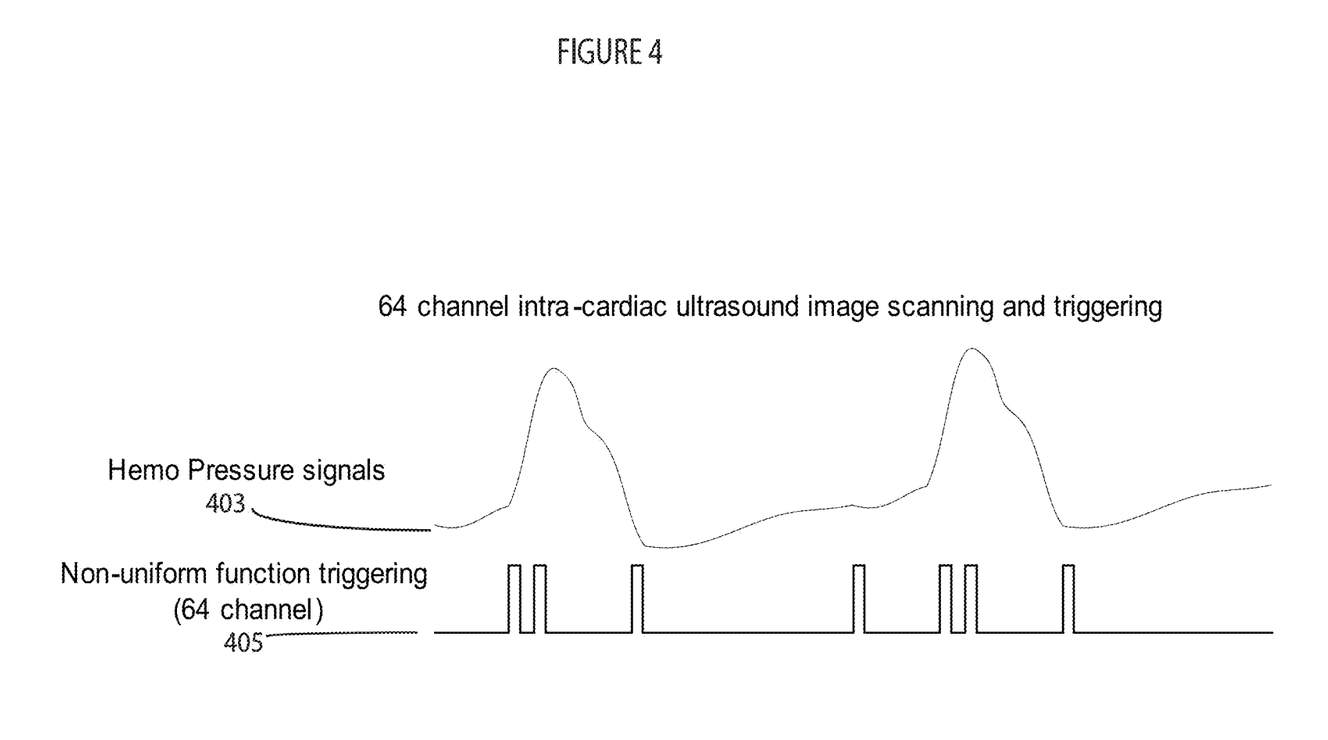
FIG. 4 illustrates multi-channel intra-cardiac ultrasound image scanning triggered in response to a cardiac function signal (such as a pressure signal), according to invention principles.
Figure 5:
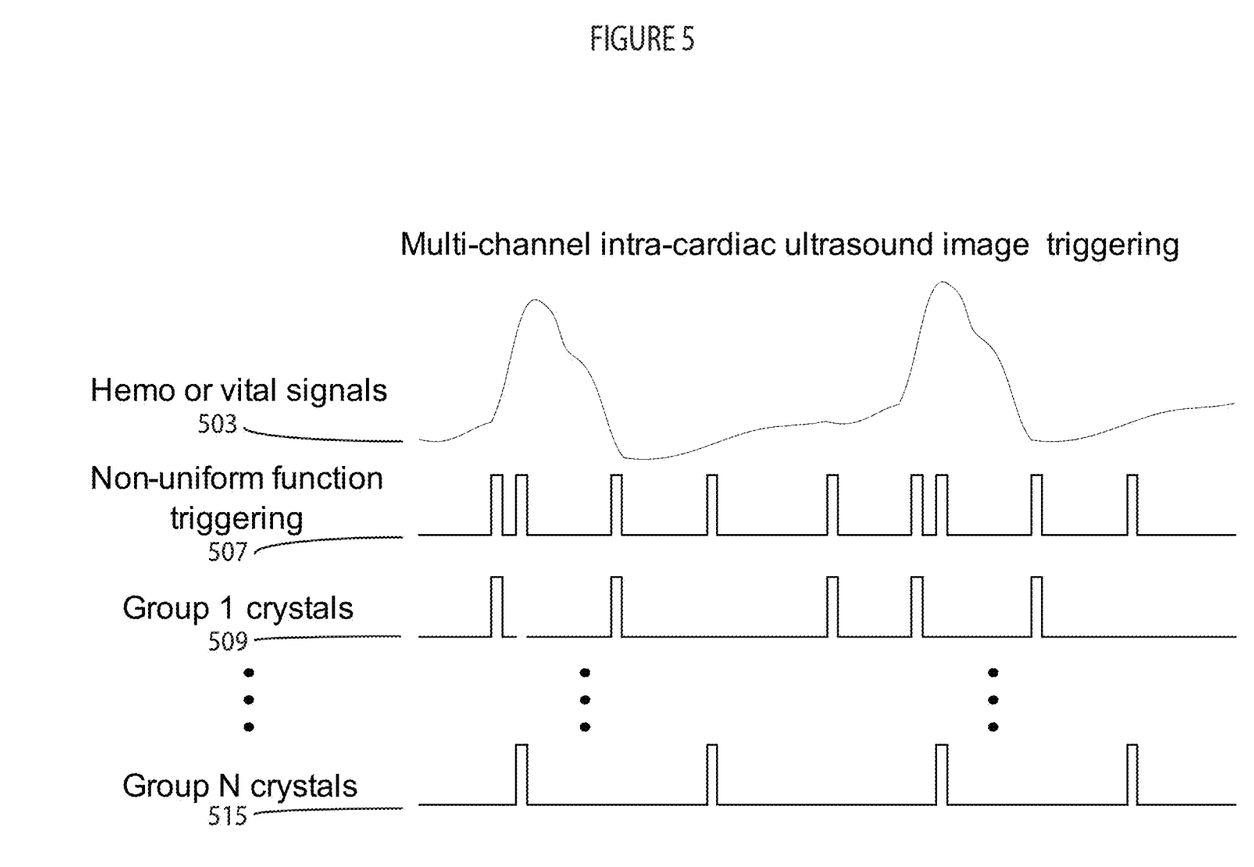
FIG. 5 illustrates non-uniform intra-cardiac ultrasound image scanning using different groups of ultrasound crystals in response to derived cardiac function signal gating pulse sequences, according to invention principles.

FIG. 4 illustrates multi-channel intra-cardiac ultrasound image scanning triggered in response to a cardiac function signal (such as an invasive pressure signal 403). System 10 optimizes ultrasound image acquisition in response to a non-uniform image triggering signal for time and spatial information capture. FIGS. 4 and 5 illustrate different kinds of non-uniform image acquisition triggering for image scanning and data acquisition using a multi-channel intra-cardiac ultrasound system employing a multi-channel crystal based intra-cardiac ultrasound catheter. Synchronization processor 19 adaptively generates a series of synchronization gating pulses 405 for corresponding heart function analysis, such as of stroke volume and cardiac output analysis and diagnosis in response to a cardiac function signal (such as pressure signal 403).

FIG. 5 illustrates non-uniform intra-cardiac ultrasound image scanning using different groups of ultrasound crystals in response to derived cardiac function signal gating pulse sequences. The multi-channel ultrasound crystals are grouped and programmed based on data identifying a clinical application and user preferences. Catheter 36 (FIG. 1) advantageously activates and triggers different group crystals 1 to N for image scanning and data acquisition in response to corresponding 1 to N cardiac function signal gating sequences 509-515 derived from hemodynamic or vital sign signals 503. Synchronization processor 19 similarly derives composite non-uniform cardiac function gating signal 507 from hemodynamic or vital sign signals 503. In catheter 36, groups of multi-channel ultrasound transducers comprising multiple individual sound generation crystals, are oriented in different kinds of direction (in increments in a range 0 to 360 degrees around the catheter), and this enables single catheter 36 to achieve real time 3D intra-cardiac mapping and image acquisition without need for additional catheter movement or twisting. For example, group 1 crystals are oriented in a designated 0 degree location on catheter 36 and are triggered by gating signal sequence 1 509 and group N crystals are oriented in a designated relative 330 degree circular location on catheter 36 and are triggered by gating signal sequence N 515. The trigger signal time stamps and corresponding acquired images may be in different cardiac cycles. In this way, a composite image is derived from information from the N transducer groups. A 3D image is reconstructed in real time from the imaging information provided by the different transducers for physician review.

Figure 6:
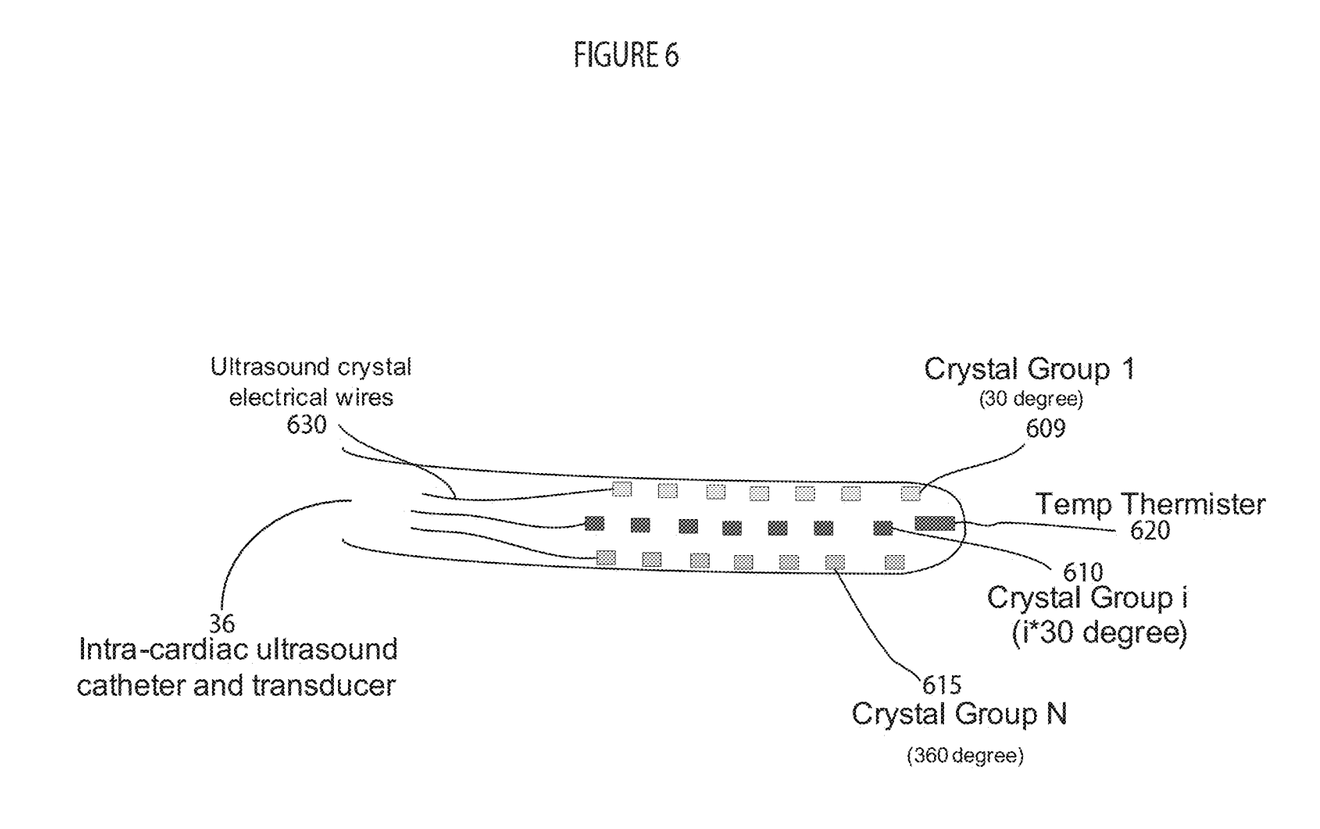
FIG. 6 shows a multi-channel ultrasound catheter with different groups of ultrasound crystals arranged at different angles on the catheter triggered by corresponding different respective pulse sequences to acquire a synchronized cardiac function image, according to invention principles.

FIG. 6 shows a multi-channel ultrasound catheter with different groups of ultrasound crystals arranged at different angles on the catheter triggered by corresponding different respective pulse sequences to acquire a synchronized cardiac function image. Catheter 36 employs N groups of crystals (N transducers) including crystal group 1 (609), crystal group i (610) and crystal group N (615) electrically powered via wires 630. A temperature measurement thermister 620 is located at the tip of catheter 36. The groups of crystals are linearly aligned along catheter 36 and in 30 degree increments around catheter 36. The N different groups of crystals 609, 610 and 615 are gated and triggered by corresponding different pulse sequences to produce a synchronized cardiac function image.

Figure 7:
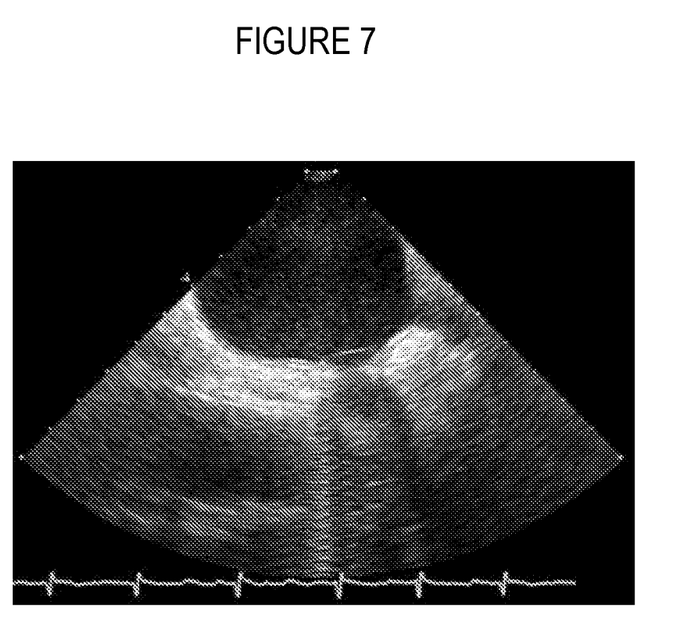
FIG. 7 shows an ultrasound image derived using combined hemodynamic and vital sign signal triggering, according to invention principles.

FIG. 7 shows an ultrasound image acquired using a non-uniform trigger signal derived by synchronization processor 19 using a combination of hemodynamic, EP and vital sign signals and data identifying a clinical application or procedure. The non-uniform triggering and gating signal, in another embodiment, may also be derived in response to electrical shock stimulation or ablation signals. Synchronization processor 19 (FIG. 1) determines an optimized time stamp and gating trigger pulse sequence used by an ultrasound image system to capture the best quality images for diagnosing a region of interest (ROI), cardiac function analysis and cardiac event prediction. The derived trigger pulse sequence reduces noise effects (blurring and distortion) and provides optimum image resolution.

Figure 8:
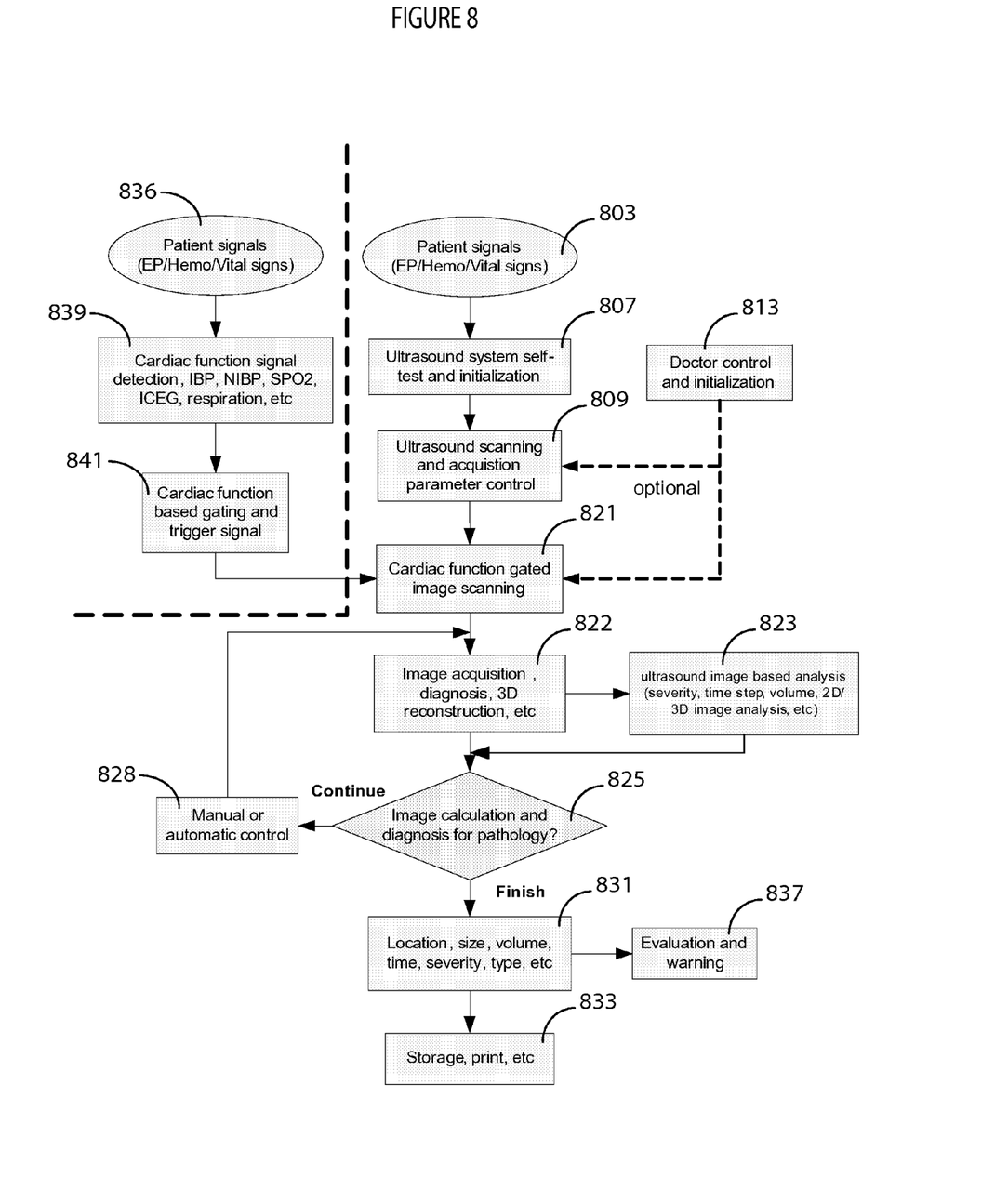
FIG. 8 shows a flowchart of a process used by an ultrasound imaging system performing cardiac function signal based patient image acquisition, according to invention principles.

FIG. 8 (FIG. 1) shows a flowchart of a process used by ultrasound imaging system 10 for performing cardiac function signal based patient image acquisition. System 10 in step 807 initializes and performs a self-test using EP, hemodynamic and vitals sign signals acquired in step 803. Acquisition parameters of ultrasound image acquisition device 15 are set in step 809. Imaging device 15 adaptively adjusts image acquisition in response to cardiac function signals to provide optimum image pixel resolution for a particular clinical application, such as maximum chamber volume estimation or motion noise rejection, for example. Imaging device 15 performs non-uniform imaging by adaptively adjusting parameters used for image acquisition, including image pixel resolution, scanning time of each image frame, image sensitivity and image system movement speed. Imaging device 15 adaptively selects different image pixel resolutions at different cardiac cycle stages in response to data identifying a clinical application. Device 15 selects high pixel resolution image acquisition during a resting stage of the heart and selects low pixel resolution image acquisition during periods of fast squeezing and contracting heart tissue. The acquired low resolution images are mapped and registered against the high resolution images to provide a high resolution MPEG compatible real time image sequence for physician review.

Ultrasound image acquisition device 15 performs ultrasound image scanning and acquisition in step 821 gated and synchronized using a trigger signal derived by synchronization processor 19 in step 841. System 10 adaptively adjusts image scanning and acquisition parameters using cardiac function based gating and synchronizing signals including a patient signal (waveform or synchronization pulse) and derived trigger signals (such as frequency, energy, spectrum, dominant time or frequency signal components). Synchronization processor 19 derives the trigger signal in step 841 using input signals provided in step 839 including cardiac hemodynamic signals (including an intra-cardiac blood pressure signal, temperature signals, a blood flow speed signal), vital signs signals (including non-invasive (and invasive) blood pressure signals, respiration signals, SPO2 signal) and cardiac electrophysiological signals (including surface ECG signals, intra-cardiac electrograms, both unipolar and bipolar signals). The input signals are acquired in step 836 and digitized and conditioned by patient monitoring system 12 and sent to imaging system 15 in step 839. System 10 tunes image scanning and acquisition based on the signals, to obtain an optimum image for a specific application such as maximum chamber volume calculation with motion noise rejection. Specifically, imaging device 15 parameters are selected in step 809 and imaging acquisition is controlled in step 821, in response to physician commands entered in step 813.

Two dimensional image data acquired in step 821 is processed in step 822 by imaging device 15 to form a 3D imaging dataset and to be suitable for automated and physician interpretation for diagnosis. In step 823 imaging device 15 selects a process to use for analysis of an acquired image to determine, medical condition, severity, time step used between image acquisitions, chamber volume and to derive a 3D image reconstruction from a 2D image, for example. Selectable processes include a process for chamber edge determination for maximum chamber area and volume analysis and image registration for vessel and chamber analysis.

In step 825 imaging device 15 performs qualitative and quantitative analysis of the dataset generated in step 822 using a process selected in step 823. Specifically, imaging device 15 performs qualitative and quantitative analysis of the dataset to identify and characterize abnormal cardiac functions and pathologies to determine image associated parameters and calculate image associated values and identify a particular medical condition by mapping determined parameters and calculated values to corresponding value ranges associated with medical conditions using mapping information in repository 17. Imaging device 15 also determines medical condition severity and chamber volume, for example. Steps 822 and 825 are iteratively repeated in response to manual or automatic direction in step 828 to identify medical condition characteristics in one or more different acquired images. In response to completion of iterative image analysis, imaging device 15 in step 831 determines location, size, volume, severity and type of medical condition as well as time within a heart cycle. Imaging device 15 initiates generation of an alert message for communication to a user in step 837 and provides medical information for use by a physician in making treatment decisions. Imaging device 15 in step 833 presents images synchronized with a synchronization signal, to a user on reproduction device 39 or a printer and stores images in repository 17.

Figure 9:
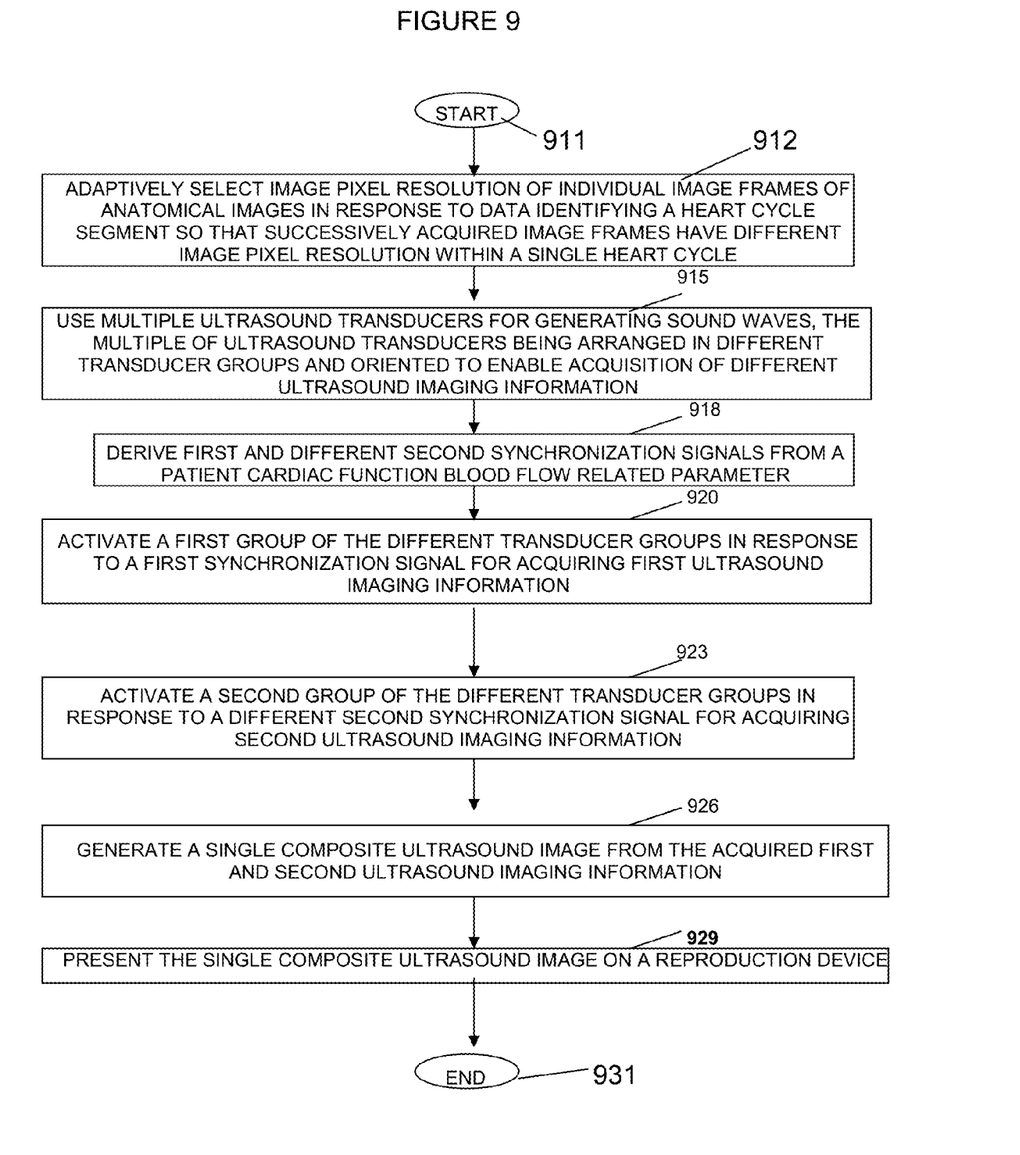
FIG. 9 shows a flowchart of a process used by an ultrasound medical imaging system for adaptively acquiring anatomical images, according to invention principles.

FIG. 9 shows a flowchart of a process used by ultrasound medical imaging system 10 (FIG. 1) for adaptively acquiring anatomical images. In step 912 following the start at step 911, image acquisition device 15 adaptively selects image pixel resolution of individual image frames of anatomical images in response to data identifying a heart cycle segment so that successively acquired image frames have different image pixel resolution within a single heart cycle. Image acquisition device 15 comprises an ultrasound image acquisition device for initiating acquisition of anatomical images of a portion of patient anatomy in response to a heart rate related synchronization signal. In step 915 device 15 uses multiple ultrasound transducers for generating sound waves in response to a control signal. The multiple ultrasound transducers are arranged in different transducer groups in catheter 36 and oriented to enable acquisition of different ultrasound imaging information.

In step 918 synchronization processor 19 derives first and different second synchronization signals using a patient cardiac function blood flow related parameter and an ECG or ICEG signal. The patient blood flow related parameter indicates at least one of, (a) invasive blood pressure, (b) non-invasive blood pressure, (c) blood flow velocity, (d) blood flow acceleration and (e) blood flow frequency. In one alternative, the heart rate related synchronization signal comprises a signal synchronized with end-diastolic pressure in a cardiac cycle and derived from a non-invasive blood pressure monitoring device or from a blood oxygen saturation (SpO2) monitoring device. In another alternative, the heart rate related synchronization signal comprises a signal synchronized with end-systolic pressure in a cardiac cycle derived from a non-invasive blood pressure monitoring device or a blood oxygen saturation (SpO2) monitoring device. In a further alternative, the synchronization signal is derived from parameter data derived from a patient blood flow related parameter comprising a blood pressure gradient indicator. Further, image acquisition device 15 acquires multiple 2D anatomical images of a patient heart in substantially the same operational phase over multiple heart beat cycles in response to a synchronization signal derived from the patient blood flow related parameter. The same operational phase comprises at least one of, (a) an end of diastolic pressure (ED) phase and (b) an end of systolic pressure (ES) phase.

Device 15 in step 920 activates a first group of the different transducer groups in response to the first synchronization signal for acquiring first ultrasound imaging information and in step 923 activates a second group of the different transducer groups in response to the different second synchronization signal for acquiring second ultrasound imaging information. In one embodiment, the first group of the different transducer groups is activated in response to a blood flow related parameter and a second group of the different transducer groups is activated in response to an ECG or ICEG signal. In step 926 device 15 generates a single composite ultrasound image from the acquired first and second ultrasound imaging information and in step 929 presents the single composite ultrasound image on reproduction device 39. The process of FIG. 9 terminates at step 931.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. System 10 automatically adaptively triggers image acquisition and selects image resolution, scanning frequency and acquisition speed of an (e.g., ultrasound) image system in response to cardiac functions and data indicating a clinical application. Further, the processes and applications may, in alternative embodiments, be located on one or more (e.g., distributed) processing devices on a network connecting the elements of FIG. 1. Any of the functions and steps provided in FIGS. 1-9 may be implemented in hardware, software or a combination of both.

What is claimed is:

1. An ultrasound medical imaging system for adaptively acquiring anatomical images, comprising:
    an ultrasound image acquisition device to acquire anatomical images of a portion of patient anatomy in response to a heart rate related synchronization signal, said ultrasound image acquisition device including a plurality ultrasound transducers to generate sound waves, said plurality of ultrasound transducers being arranged in different transducer groups each comprising a plurality of the ultrasound transducers configured at different angle orientations in increments in a range of 0 to 360 degrees around the ultrasound image acquisition device to enable 360 degree acquisition of different ultrasound imaging information at a same particular time within a same heart cycle to generate a single composite ultrasound image without a need to move the ultrasound image acquisition device;
    a synchronization processor for deriving said synchronization signal from a combination of at least one hemodynamic signal representative of a patient cardiac function blood flow related parameter and other patient monitoring signals, said synchronization signal enabling adaptive activation of a particular group of said different transducer groups for acquisition ultrasound imaging information at the same particular time within a same heart cycle to generate said single composite ultrasound image,
    wherein said synchronization processor provides a heart-rate related synchronization signal derived from said at least one hemodynamic signal representative of a patient cardiac function blood flow related parameter and other patient monitoring signals including an ECG (electrocardiogram) or ICEG (intra-cardiac electrogram) signal and a first group of said different transducer groups is activated in response to said at least one hemodynamic signal representative of a blood flow related parameter and a second group of said different transducer groups is activated in response to said ECG or ICEG signal;
    and a display processor for presenting said single composite ultrasound image, acquired by said ultrasound image acquisition device, to a user on a reproduction device.

2. A system according to claim 1, wherein said image acquisition device adaptively selects image pixel resolution of individual image frames of said anatomical images in response to data identifying a heart cycle segment to acquire successive image frames have different image pixel resolutions within a single heart cycle.

3. A system according to claim 1, wherein said heart-rate related synchronization signal comprises a signal synchronized with end-diastolic pressure in a cardiac cycle.

4. A system according to claim 3, wherein the end-diastolic pressure synchronized signal is derived from a non-invasive blood pressure monitoring device.

5. A system according to claim 3, wherein the end-diastolic pressure synchronized signal is derived from a blood oxygen saturation (SpO2) monitoring device.

6. A system according to claim 1, wherein said heart-rate related synchronization signal comprises a signal synchronized with end-systolic pressure in a cardiac cycle.

7. A system according to claim 6, wherein the end-systolic pressure synchronized signal is derived from a non-invasive blood pressure monitoring device.

8. A system according to claim 7, wherein the end-systolic pressure synchronized signal is derived from a blood oxygen saturation (SpO2) monitoring device.

9. A system according to claim 1, wherein said at least one hemodynamic signal representative of patient blood flow related parameter indicates at least one of, (a) invasive blood pressure, (b) non-invasive blood pressure, (c) blood flow velocity, (d) blood flow acceleration and (e) blood flow frequency.

10. A system according to claim 1, wherein said synchronization signal is derived from parameter data derived from said at least one hemodynamic signal representative of a patient blood flow related parameter.

11. A system according to claim 10, wherein said parameter data derived from said patient blood flow related parameter is a blood pressure gradient indicator.

12. A system according to claim 1, wherein said image acquisition device acquires a plurality of 2D anatomical images of a patient heart in substantially the same operational phase over a, plurality of heartbeat cycles in response to said synchronization signal derived from said from said at least one hemodynamic signal representative of patient blood flow related parameter.

13. A system according to claim 12, wherein said same operational phase comprises at least one of, (a) an end of diastolic pressure (ED) phase and (b) an end of systolic pressure (ES) phase.

14. A system according to claim 1, wherein said plurality of ultrasound transducers generate sound waves in response to a control signal.

15. An ultrasound medical imaging system for adaptively acquiring anatomical images, comprising: an ultrasound image acquisition device to acquire anatomical images of a portion of patient anatomy, said ultrasound image acquisition device including a plurality of ultrasound transducers to generate sound waves and a first group of said plurality of ultrasound transducers being activated in response to a first synchronization signal and a second group of said different transducer groups is activated in response to a different second synchronization signal, said plurality of ultrasound transducers being arranged in different transducer groups and each comprising a plurality of the ultrasound transducers configured at different angle orientations in increments in a range of 0 to 360 degrees around the ultrasound image acquisition device to enable 360 degree acquisition of different ultrasound imaging information at a same particular time within a same heart cycle to generate a single composite ultrasound image without a need to move the ultrasound image acquisition device;

a synchronization processor for deriving said synchronization signals from a combination of at least one hemodynamic signal representative of a patient cardiac function blood flow related parameter and other patient monitoring signals, said synchronization signal enabling adaptive activation of a particular group of said different transducer groups for acquisition of ultrasound imaging information to generate said single composite ultrasound image,     wherein said synchronization processor provides a heart-rate related synchronization signal derived from said at least one hemodynamic signal representative of a patient cardiac function blood flow related parameter and other patient monitoring signals including an ECG (electrocardiogram) or ICEG (intra-cardiac electrogram) signal and a first group of said different transducer groups is activated in response to said at least one hemodynamic signal representative of a blood flow related parameter and a second group of said different transducer groups is activated in response to said ECG or ICEG signal;

and a display processor for presenting said single composite ultrasound image, acquired by said ultrasound image acquisition device, to a user on a reproduction device.

16. A system according to claim 15, wherein said image acquisition device adaptively selects image pixel resolution of individual image frames of said anatomical images in response to data identifying a heart cycle segment to acquire successive image frames having different image pixel resolutions within a single heart cycle.

\* \* \* \* \*